United States Patent
Cohen et al.

(10) Patent No.: US 10,463,445 B2
(45) Date of Patent: Nov. 5, 2019

(54) POINT DENSITY ILLUSTRATION

(71) Applicant: Biosense Webster (Israel) Ltd., Yokneam (IL)

(72) Inventors: Assaf Cohen, Kiryat Bialik (IL); Fady Massarwi, Baka Al Gharbiyya (IL); Ido Ilan, Yoqneam (IL); Itai Doron, Katsir (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 25 days.

(21) Appl. No.: 15/822,380

(22) Filed: Nov. 27, 2017

(65) Prior Publication Data

US 2019/0159861 A1    May 30, 2019

(51) Int. Cl.
| | |
|---|---|
| *A61B 90/00* | (2016.01) |
| *G06T 17/00* | (2006.01) |
| *G06T 11/40* | (2006.01) |
| *A61B 34/10* | (2016.01) |
| *G06T 19/20* | (2011.01) |

(Continued)

(52) U.S. Cl.
CPC ............. *A61B 90/37* (2016.02); *A61B 34/10* (2016.02); *G06T 11/40* (2013.01); *G06T 17/00* (2013.01); *G06T 19/20* (2013.01); *A61B 5/042* (2013.01); *A61B 5/062* (2013.01); *A61B 5/063* (2013.01); *A61B 2017/00053* (2013.01); *A61B 2017/00199* (2013.01); *A61B 2034/105* (2016.02); *G06T 2210/41* (2013.01); *G06T 2219/2004* (2013.01)

(58) Field of Classification Search
CPC ... A61B 90/37; A61B 34/10; A61B 2034/105; A61B 2017/00053; A61B 2017/00199; A61B 5/063; A61B 5/062; A61B 5/042; G06T 19/20; G06T 17/00; G06T 2219/2004; G06T 2210/41
See application file for complete search history.

(56) References Cited

U.S. PATENT DOCUMENTS

| | | |
|---|---|---|
| 5,391,199 A | 2/1995 | Ben-Haim |
| 5,443,489 A | 8/1995 | Ben-Haim |

(Continued)

FOREIGN PATENT DOCUMENTS

| | | |
|---|---|---|
| EP | 2395481 A2 | 12/2011 |
| EP | 2837328 A1 | 2/2015 |
| WO | 2007/035306 A2 | 3/2007 |

OTHER PUBLICATIONS

Bernardini et al. "The Ball-Pivoting Algorithm for Surface Reconstruction", IEEE Transactions on Visualization and computer Graphics, vol. 5, Issue 4, Oct. 1999, pp. 349-359 (Year: 1999).*

(Continued)

*Primary Examiner* — Michael Le
(74) *Attorney, Agent, or Firm* — Notaro, Michalos & Zaccaria P.C.

(57) ABSTRACT

Methods, computing systems and computer software products implement embodiments of the present invention that include receiving, by a processor, respective coordinates for multiple points on a surface, and rendering an image of the surface on a display screen. For each given point among the multiple points, a density of the points within a region surrounding the given point is computed, and the given point on the surface with a point size that is inversely related to the computed density is rendered on the display screen.

17 Claims, 4 Drawing Sheets

(51) Int. Cl.
  *A61B 5/042* (2006.01)
  *A61B 5/06* (2006.01)
  *A61B 17/00* (2006.01)

(56) References Cited

U.S. PATENT DOCUMENTS

| | | | |
|---|---|---|---|
| 5,558,091 | A | 9/1996 | Acker |
| 6,172,499 | B1 | 1/2001 | Ashe |
| 6,177,792 | B1 | 1/2001 | Govari |
| 6,263,287 | B1 | 7/2001 | Zheng |
| 6,690,963 | B2 | 2/2004 | Ben-Haim |
| 6,788,967 | B2 | 9/2004 | Ben-Haim |
| 6,975,335 | B2 | 12/2005 | Watanabe |
| 7,046,247 | B2 | 5/2006 | Hao |
| 9,299,186 | B2 | 3/2016 | Shoemaker |
| 9,323,413 | B2 | 4/2016 | Baar |
| 9,757,044 | B2 * | 9/2017 | Scharf .................. A61B 5/0422 |
| 2001/0009974 | A1 * | 7/2001 | Reisfeld ............. A61B 5/04011 600/407 |
| 2012/0330636 | A1 * | 12/2012 | Albou .................... G16B 15/00 703/12 |
| 2018/0221075 | A1 * | 8/2018 | Warner ................ A61B 5/4848 |

OTHER PUBLICATIONS

Bernardini et al. "The Ball-Pivoting Algorithm for Surface Reconstruction", IEEE Transactions on Visualization and computer Graphics, vol. 5, Issue 4, Oct. 1999, pp. 349-359 (Year: 1999) (Year: 1999).*

Bernardini et al. "*The Ball-Pivoting Algorithm for Surface Reconstruction*", IEEE Transactions on Visualization and computer Graphics, vol. 5, Issue 4, Oct. 1999, pp. 349-359.

Wilson, Kevin, "Mapping of Cardiac Electrophysiology Onto a Dynamic Patient-Specific Heart Model", IEEE Transactions on Medical Imaging, IEEE Service Center, Piscataway, NJ, US, vol. 28, No. 12, Dec. 1, 2009, pp. 1870-1880, XP011281238, ISSN: 0278-0062.

Extended European search report for corresponding European patent application No. EP 18208351.9, dated Mar. 4, 2019.

* cited by examiner

FIG. 3

POINT DENSITY ILLUSTRATION

FIELD OF THE INVENTION

The present invention relates generally to image presentation, and specifically to presenting an image of a surface comprising multiple mapping points.

BACKGROUND OF THE INVENTION

Some medical procedures include mapping a cavity of a body organ such as a heart. To map the cavity, an operator positions a medical probe at specific locations within the organ, and the probe measures and conveys location information to a mapping system. The mapping system generates a map comprising the measured locations in the organ. The map can be used in applying various diagnostic and therapeutic procedures to the organ.

U.S. Pat. No. 6,975,335 to Watenabe describes a method for displaying magnified and reduced areas. The method includes changing pattern densities of areas in an image in order to enable easy detection of magnified and/or reduced areas. For example, when a first given area is magnified and displayed, and a second given area is reduced as a result, a pattern of the first given area is magnified and displayed while a pattern of the second given area is reduced and displayed with respect to the other portions of the image.

U.S. Pat. No. 7,046,247 to Hao et al., describes a method for visualizing graphical data sets having a non-uniform graphical density for display. The method includes determining graphical densities of regions and presenting regions having higher graphical densities at higher resolutions.

Chapter 28 in the Handbook of Computational Statistics: Concepts and Methods (Gentle, James et al., Springer, 2012) includes a description of a method for presenting data points plotted in a graph. The method includes increasing a brightness parameter for data points in areas with relatively high overplotting (i.e., areas comprising high densities of data points).

U.S. Pat. No. 9,323,413 to Baar et al., describes a graphical user interface (GUI) with zoom for detail-in-context presentations. The GUI includes a "lens region" that includes a "focal region" surrounded by a "shoulder region". The focal region is presented using high magnification, and information in the "shoulder region" is visibly compressed.

U.S. Pat. No. 9,299,186 to Shoemaker et al., describes a method for presenting a region-of-interest of an original image. In the method, the original image can be a mesh comprising a collection of polygons having polygons defined by three or more shared edges joined at vertex points.

U.S. Pat. No. 6,263,287 to Zhen et al., describes a method for manipulating and analyzing gene expression data. The method includes graphical tools, and uses a clustering algorithm to correlate temporal patterns of gene expression.

The description above is presented as a general overview of related art in this field and should not be construed as an admission that any of the information it contains constitutes prior art against the present patent application.

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

SUMMARY OF THE INVENTION

There is provided, in accordance with an embodiment of the present invention, a method, including receiving, by a processor, respective coordinates for multiple points on a surface, rendering an image of the surface on a display screen, and for each given point among the multiple points, computing a density of the points within a region surrounding the given point, and rendering, on the display screen, the given point on the surface with a point size that is inversely related to the computed density.

In some embodiments, computing the density of the points within the region surrounding the given point includes counting a number of the points within the region. In other embodiments, computing the density of the given point within the region includes identifying, from the multiple points, a further point that is closest to the given point, and determining a distance between the given point and the further point.

In additional embodiments, the surface comprises a two-dimensional surface or a three-dimensional surface. In further embodiments, the three-dimensional surface is representative of tissue in a body cavity, and wherein receiving the respective coordinates comprises receiving the respective coordinates from a medical probe inserted into the body cavity. In supplemental embodiments, the body cavity includes a heart, wherein the tissue comprises intracardiac tissue, and wherein the medical probe comprises an intracardiac catheter.

In some embodiments, rendering the given point includes presenting, on the display, the given point using a shape selected from a group consisting of a circle, an oval and a star. In additional embodiments, computing the density of the points within the region surrounding the given point includes defining each given region as a sphere comprising a center having a center corresponding to the coordinates of the given point and a radius having a specified length. In further embodiments, the method includes defining multiple visual effects, assigning each of the visual effects to a respective range of the densities, and rendering, on the display, the given point on the surface with a given visual effect that is based on the computed density.

There is also provided, in accordance with an embodiment of the present invention, an apparatus, including a display screen, and a processor configured to receive respective coordinates for multiple points on a surface, to render an image of the surface on the display screen, and for each given point among the multiple points, to compute a density of the points within a region surrounding the given point, and to render, on the display screen, the given point on the surface with a point size that is inversely related to the computed density.

There is further provided, in accordance with an embodiment of the present invention, a computer software product the product including a non-transitory computer-readable medium, in which program instructions are stored, which instructions, when read by a computer, cause the computer to receive respective coordinates for multiple points on a surface, to render an image of the surface on a display screen, and for each given point among the multiple points, to compute a density of the points within a region surrounding the given point, and to render, on the display screen, the given point on the surface with a point size that is inversely related to the computed density.

BRIEF DESCRIPTION OF THE DRAWINGS

The disclosure is herein described, by way of example only, with reference to the accompanying drawings, wherein.

DETAILED DESCRIPTION OF EMBODIMENTS

Overview

Anatomical mapping procedures typically create a map comprising map points collected from a mapping system. Each map point (also referred to herein simply as a point) comprises a respective coordinate within a body cavity, and possibly a physiological property collected by a medical probe at the respective coordinate. While collecting the map points, some of the points may be close to each other, defining dense regions. Other points may be far from all other points, and these points are assumed to define sparse regions. While a user typically wants to reduce or eliminate sparse regions while mapping a body cavity, it may be difficult for the user to identify the sparse regions while performing the procedure.

As described supra, a dense region comprises map points that are close to one another. If the map points in a dense region are presented using the same size, it may be difficult for a user to differentiate between them, especially if there are overlapping and/or completely hidden map points. Therefore, it may be difficult for a user to identify a specific map point in a dense region.

Embodiments of the present invention provide methods and systems for emphasizing points in sparse regions while mapping a body cavity such as a heart. As described hereinbelow, respective coordinates are received for multiple points on a surface, and an image of the surface is rendered on a display screen. For each given point among the multiple points, a density of the points within a region surrounding the given point is computed, wherein the given point on the surface is rendered with a point size that is inversely related to the computed density.

By rendering points with point sizes that are inversely related to the densities of their respective regions, systems implementing embodiments of the present invention can present larger-sized points in sparse regions, and can present smaller-sized points in dense regions. Consequently, points defining sparse regions can be emphasized (i.e., by their larger-sized points), thereby enabling a user to easily identify any sparse regions in the map. Likewise, using smaller sizes to present map points in a dense region enables a user to easily distinguish between the individual map points in the region.

System Description

Figure 1:
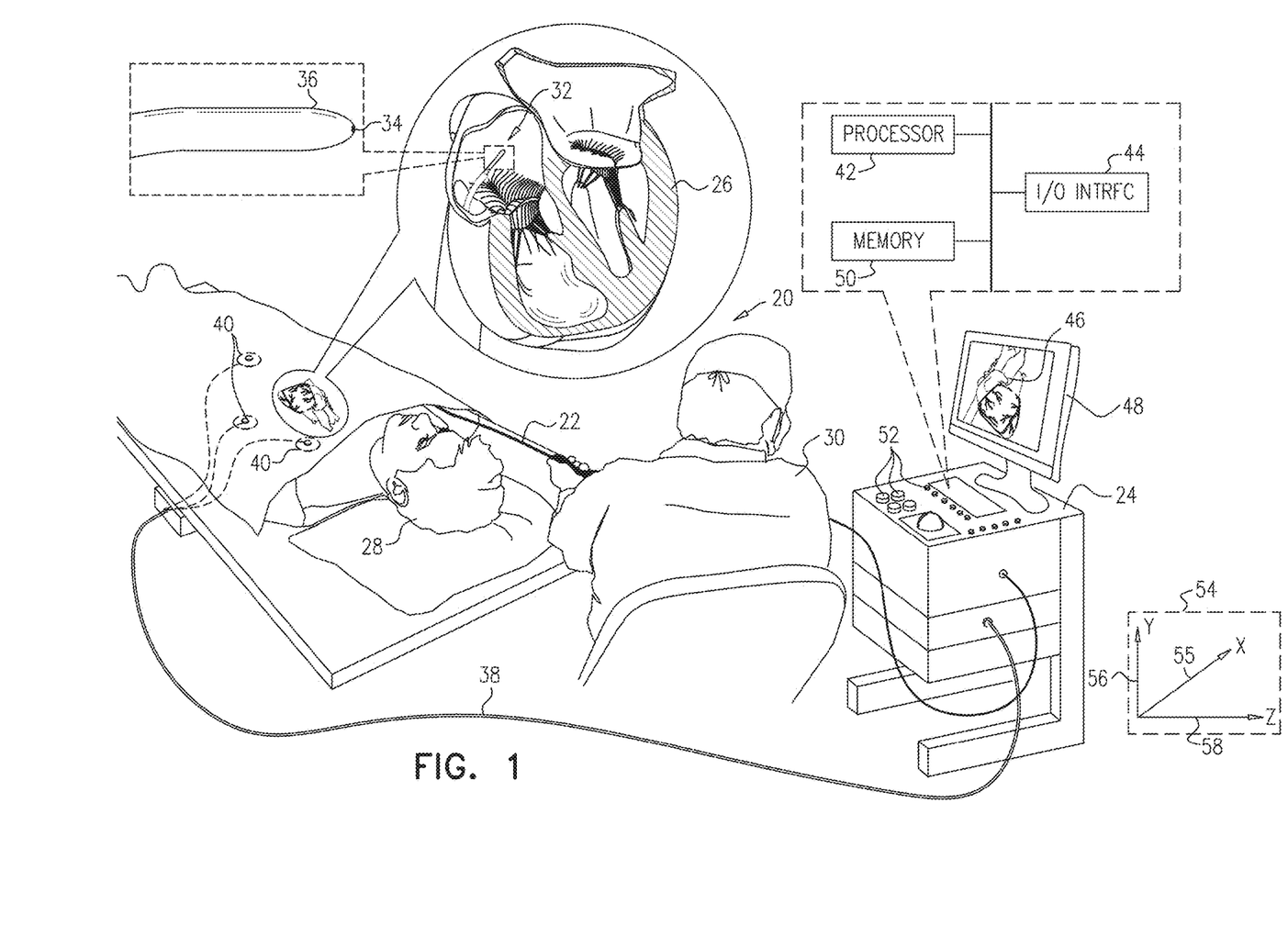
FIG. 1 is a schematic pictorial illustrations of a medical system configured to adjust sizes of points in a map based on densities of regions in the map including the points, in accordance with an embodiment of the present invention.

FIG. 1 is a schematic, pictorial illustration of a medical system 20 comprising a medical probe 22 and a control console 24, in accordance with an embodiment of the present invention. Medical system 20 may be based, for example, on the CARTO® system, produced by Biosense Webster Inc. (33 Technology Drive, Irvine, Calif. 92618). In embodiments described hereinbelow, medical probe 22 comprises an intracardiac catheter that is used for mapping a heart 26 of a patient 28. Alternatively, medical probe 22 may be used, mutatis mutandis, for other therapeutic and/or diagnostic purposes in the heart or in other body organs.

During a medical procedure, a medical professional 30 inserts medical probe 22 into a biocompatible sheath (not shown) that has been pre-positioned in a body cavity (e.g., a chamber of heart 26) of the patient so that a distal end 32 of the medical probe enters the body cavity. In the configuration shown in FIG. 1, a probe electrode 34 is mounted on a distal tip 36 of medical probe 22. The probe electrode typically comprises a thin metal layer formed over distal tip 36. In some embodiments, distal end 32 may have other electrodes that are insulated from each other and from electrode 34, which for simplicity are not shown in the diagram. Electrode 34 is connected to control console by conductors in probe 22, not shown in the figures.

In embodiments described herein, electrode 34 can be used to determine a location of distal tip 36 in heart 26. In additional embodiments, electrode 34 can also be used to measure a certain physiological property (e.g., the local surface electrical potential) at multiple locations in heart 26.

Control console 24 is connected, by a cable 38, to body surface electrodes, which typically comprise adhesive skin patches 40 that are affixed to patient 28. Control console 24 comprises a processor 42 that can determine position coordinates of distal tip 36 inside heart 26 based on impedances measured between adhesive skin patches 40 and probe electrode 34.

To determine the position of distal tip 36, control console 24 can convey a current to electrode 34, and processor 42 receives signals indicating respective impedances that are detected by patches 40 in response to the conveyed current. Based on the impedances, processor 42 can determine a 3D location of electrode 34 (i.e., with respect to patches 40) in a coordinate system 54 comprising an X-axis 55, a Y-axis 56 and a Z-axis 58. Impedance-based position tracking techniques are described, for example, in U.S. Pat. Nos. 5,983,126, 6,456,864 and 5,944,022, whose disclosures are incorporated herein by reference.

Figure 2:
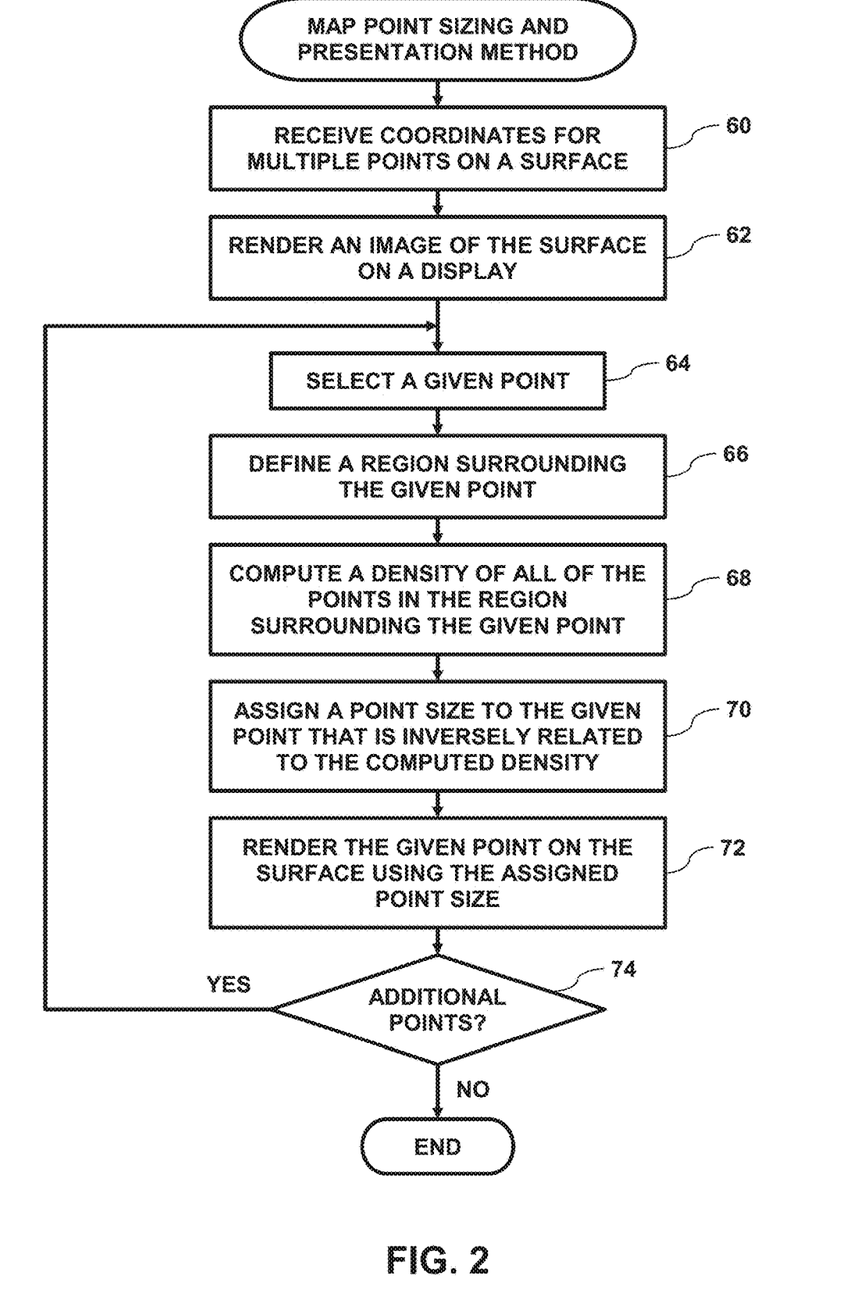
FIG. 2 is a flow diagram that schematically illustrates a method of presenting the map comprising points having different sizes, in accordance with an embodiment of the present invention.

Although the medical system shown in FIGS. 1 and 2 uses impedance-based sensing to measure a location of distal tip 36, other position tracking techniques may be used (e.g., techniques using magnetic-based sensors). In systems using magnetic-based sensors, distal end 32 comprises a magnetic field sensor (not shown) typically comprising a set of three orthogonal sensor coils, and generator coils (not shown) are placed below the patient at known positions external to patient 28. The generator coils transmit alternating magnetic fields into a region within patient 28, the alternating magnetic fields induce signals in the magnetic field sensor, and processor 42 analyzes these signals to derive the location and orientation of the magnetic field sensor with respect to the field generator coils.

Magnetic position tracking techniques are described, for example, in U.S. Pat. Nos. 5,391,199, 5,443,489, 6,788,967, 6,690,963, 5,558,091, 6,172,499 6,177,792, whose disclosures are incorporated herein by reference. The methods of position sensing described hereinabove are implemented in the above-mentioned CARTO® system and are described in detail in the patents cited above.

Processor 42 typically comprises a general-purpose computer, with suitable front end and interface circuits for receiving signals from elements of medical probe 22 (e.g., probe electrode 34) and controlling the other components of control console 24. Processor 42 may be programmed in software to carry out the functions that are described herein. The software may be downloaded to control console 24 in electronic form, over a network, for example, or it may be provided on non-transitory tangible media, such as optical, magnetic or electronic memory media. Alternatively, some or all of the functions of processor 42 may be carried out by dedicated or programmable digital hardware components.

Control console 24 also comprises an input/output (I/O) communications interface 44 that enables the control console to transfer signals from, and/or transfer signals to probe electrode 34 and adhesive skin patches 40. Probe electrode 34, and processor 42 are all coupled to I/O communications interface 44 via wired connections (not shown) and/or wireless connections.

Based on impedances derived from signals received from probe electrode 34 and adhesive skin patches 40, processor 42 can generate a map 46 comprises multiple map points, with each map point comprising coordinates on an inner chamber surface of heart 26. During the procedure, processor 42 can present map 46 to medical professional 30 on a display screen 48, and store data representing the map in a memory 50. Memory 50 may comprise any suitable volatile and/or non-volatile memory, such as random access memory or a hard disk drive.

In some embodiments, medical professional 30 can manipulate map 46 using one or more input devices 52. In alternative embodiments, display 48 may comprise a touchscreen that can be configured to accept inputs from medical professional 30, in addition to presenting map 46.

Density-Based Map Point Sizing

Figure 3:
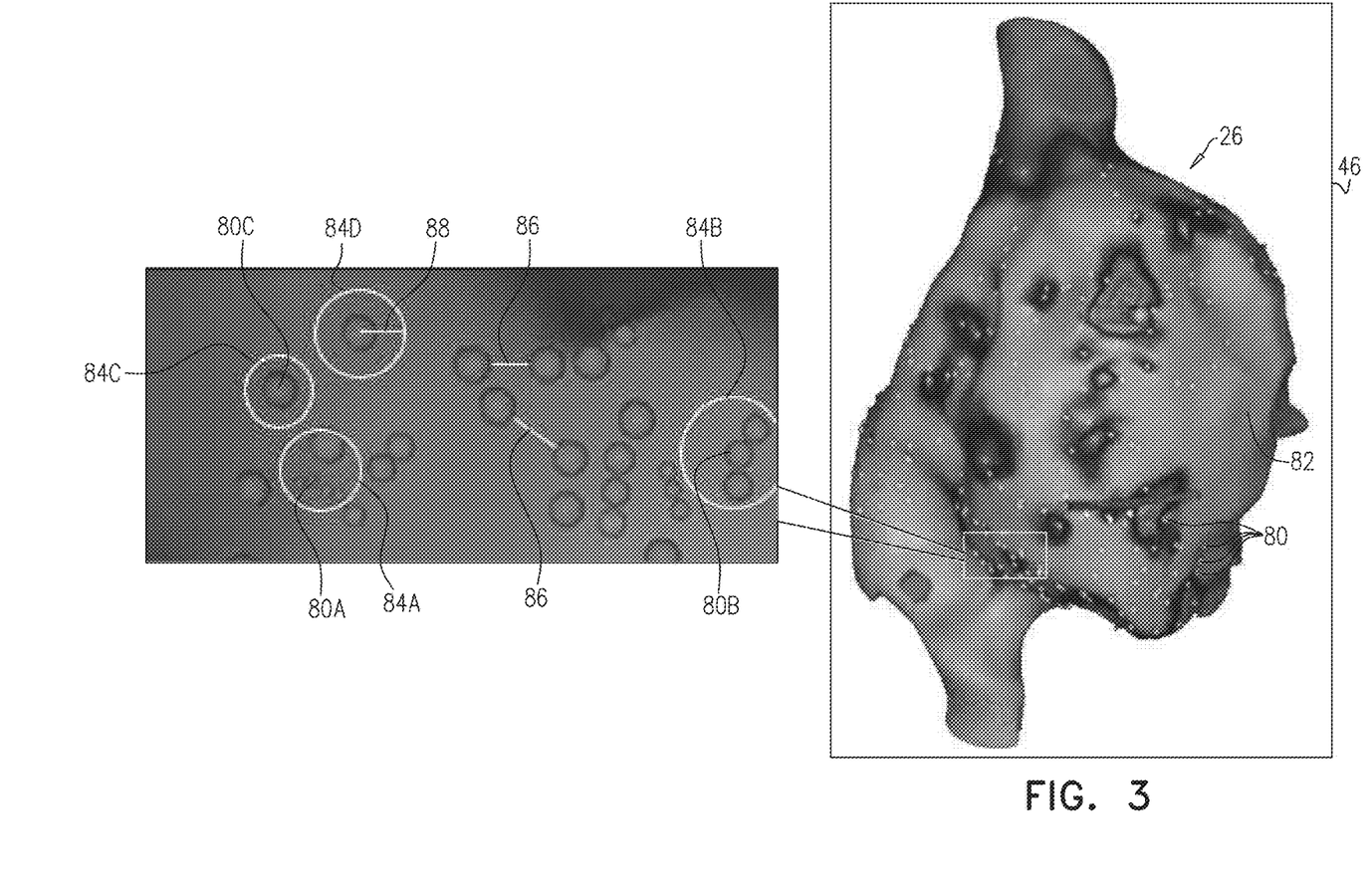
FIG. 3 is a schematic pictorial illustration showing a section of the map that includes some of the points having different sizes, in accordance with a first embodiment of the present invention.

FIG. 2 is a flow diagram that schematically illustrates a method of generating map 46, in accordance with an embodiment of the present invention, and FIG. 3 is a schematic pictorial illustration of the map comprising map points 80 having different respective density-based sizes, in accordance with a first embodiment of the present invention. In a receive step 60, processor 42 receives coordinates (i.e., in coordinate system 54) for multiple map points 80 on a surface such as tissue in heart 26, and in a first rendering step 62, the processor renders, in map 46 (i.e., on display 48), surface 82 (FIG. 3) based on the received map point coordinates.

In one embodiment, surface 82 comprises a two-dimensional (2D) surface, such as a 2D scatter plot. In another embodiment, surface 82 comprises a three-dimensional (3D) surface, such as intracardiac tissue in heart 26. An example of an algorithm that processor 42 can use to render surface 82 is described in "The Ball-Pivoting Algorithm for Surface Reconstruction" (Bernardini et al, IEEE Transactions on Visualization and Computer Graphics, Volume 5 Issue 4, October 1999, Pages 349-359), which is incorporated herein by reference. As described in the research paper, the ball pivoting algorithm computes a triangle mesh by creating a set of triangles that use map points as vertices of the triangles. Processor 42 then covers the mesh, using any convenient method known in the art, to produce surface 82.

In a selection step 64, processor 42 selects a given map point 80, and in a definition step 66, the processor defines a region 84 that surrounds the given point. In FIG. 3, regions 84 can be differentiated by appending a letter to the identifying numeral so that the regions comprise regions 84A-84D. In some embodiments, the regions are spheres (e.g., spherical regions presented as two-dimensional circles in FIG. 3), and processor 42 defines a given region 84 (e.g., region 84D in FIG. 3) around a given map point 80 by defining, in coordinate system 54, a three-dimensional sphere comprising a center corresponding to the coordinates of the given mapping point and a radius 88 having a specified length.

In one embodiment, processor 42 can define the spheres with a radius having a specific length. For example, the radius can be a fixed length between 10 and 20 millimeters. In another embodiment, processor 42 can vary the radius based on the density of the map points near the center of the sphere. For example, processor 42 can determine the geodesic distance to the closest point 80 (i.e., from the center). In this embodiment, the density is directly related to the distance from the center of the sphere to the closest point.

In a computation step 68, processor 42 computes a density of the points within the given region, and in an assignment step 70, the processor assigns, to the given point, a point size that is inversely related to the computed density. In other words, processor 42 will assign smaller point sizes to the points in the regions having higher densities, and the processor will assign larger point sizes to the points in the regions having lower densities.

In a first embodiment, processor 42 computes a given density for a given region 84 based on (e.g., by counting) a number of map points 80 within the given region. In the first embodiment, the computed density for the given map point in a given region 84 is directly related to the number of the map points in the given region (i.e., the regions having higher numbers of mapping points have higher densities and the regions having fewer number of mapping points have lower densities).

In a second embodiment, processor 42 computes respective distances 86 between pairs of map points 80, and processor 42 computes the density for a first given map point 80 by identifying a closest second given map point 80. In the second embodiment, the computed density is inversely related to the distance between the first and the second given map points (i.e., longer distances indicate lower densities and shorter distances indicate higher densities).

In a second rendering step 72, processor 42 renders, typically by superimposing, in map 46, the given map point on surface 82. To render the given map point on surface 82, processor 42 can present, on display 48, the given map point with its respective size at a location on surface 82 corresponding to the respective coordinates of the given map point. In the embodiment presented in FIG. 3, processor 42 renders map points 80 by presenting the map points as circular/oval shapes in map 46 on display 48.

In FIG. 3, map points 80 can be differentiated by appending a letter to the identifying numeral so that the map points comprise map points 80A-80C. In this example of map 46:

Region 84A has a high density and processor 42 renders map point 80A using a small sized circle.

Region 84C has a low density and processor 42 renders map point 80C using a large sized circle.

Region 84B has a medium density (i.e., between the low and the high densities), and processor 42 renders map point 80B using a medium sized circle (i.e., having a diameter between the diameter of the small and the diameter of the large sized circles).

Figure 4:
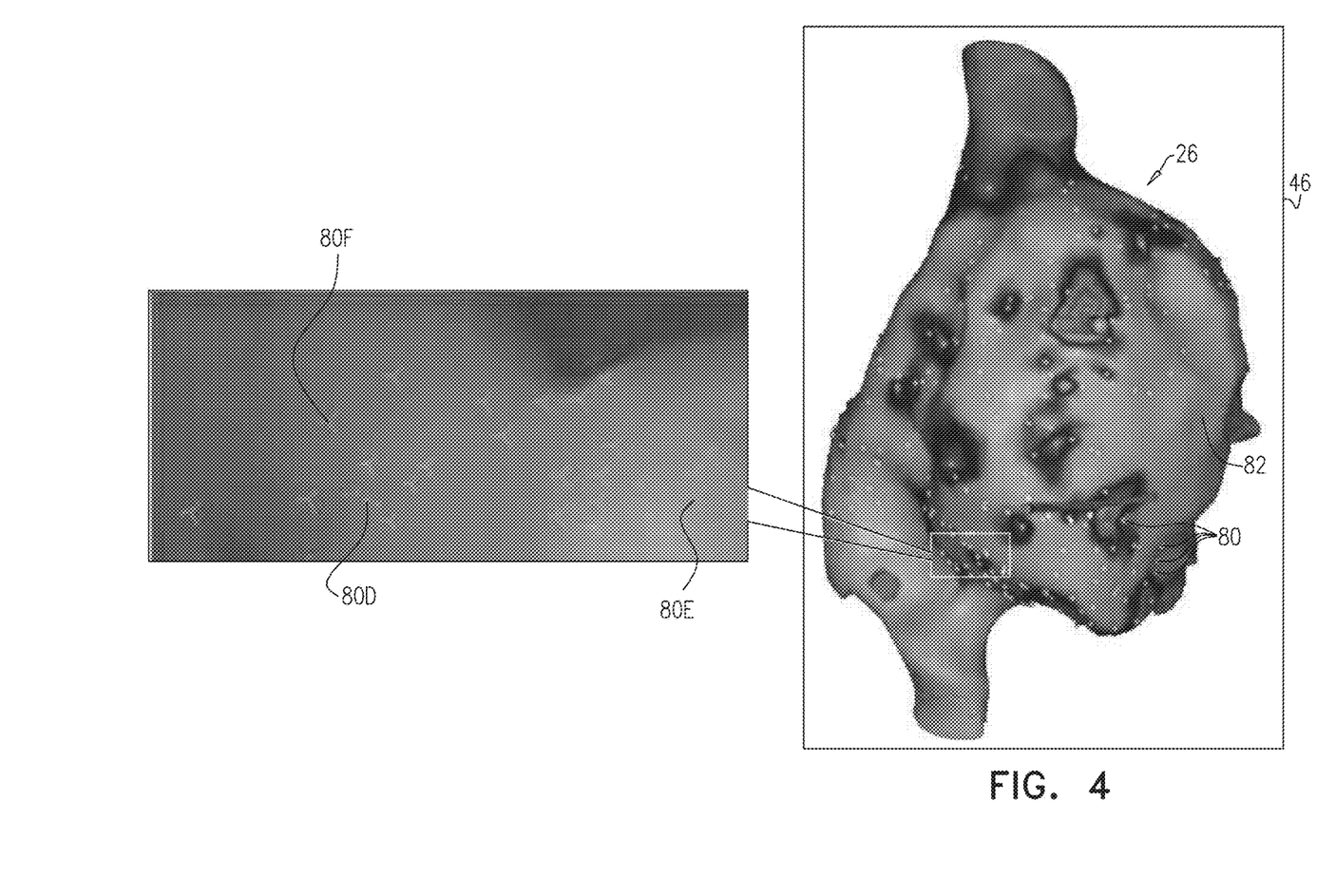
FIG. 4 is a schematic pictorial illustration showing a section of the map that includes some of the points having different sizes, in accordance with a second embodiment of the present invention.

FIG. 4 is a schematic pictorial illustration of the map comprising map points 80 having different respective density-based sizes, in accordance with a second embodiment of the present invention. In the second embodiment, processor 42 presents map points 80 as three-pointed stars having different sizes based on the respective densities of the regions containing the map points.

In the example shown in FIG. 4, the map points can be differentiated by appending a letter to the identifying numeral so that the map points comprise map points 80D-80F. As shown in FIG. 4:

Processor 42 renders map point 80D using a small sized star.

Processor 42 renders map point 80F using a large sized star.

Processor 42 renders map point 80E using a medium sized star (i.e., between the small and the large sized stars).

During a medical procedure, medical professional 30 can manipulate input devices 50 in order to set zoom levels for map 46 on display 48, thereby changing the sizes of map points 80 on the display. In some embodiments, processor 42 can define a base diameter (or radius) for map points 80, and assign respective multiples of the base diameter each of the map points. Referring to the example shown in FIG. 4, processor 42 can present map point 80F as a star with the base diameter, present map point 80E as a star with 75% of the base diameter, and map point 80D as a star with 50% of the base diameter. Therefore, as medical professional selects different zoom levels, processor 42 can present map points 80 with different diameters, but maintain the proportional lengths of the respective diameters of the map points.

In addition to presenting map points 80 as different sized ovals/circles and stars, processor 42 can use other types of visual effects to present map points 80 in regions 84 having different densities. To present map points 80 in regions 84 having different densities, processor 42 can define multiple visual effects, assign each of the visual effects to a respective range of the densities, and render, on display 48, points 80 (i.e., on map 46) with respective visual effects that are based on the respective computed densities.

In a first embodiment, processor 42 can use different colors to present map points 80. For example, processor 42 can present blue map points 80 in a dense region 84, and present red map points 80 in a sparse region 84. In a second embodiment, processor 42 can use different shapes to present map points 80. For example, processor 42 can present triangle-shaped map points 80 in a dense region 84, and present square-shaped map points 80 in a sparse region 84. In a third embodiment, processor 42 can use different visual effects when presenting map points 80. For example, processor 42 can present non-blinking map points 80 in a dense region 84, and present blinking map points 80 in a sparse region 84.

In a comparison step 74, if there are additional map points 80 that have not been sized and rendered, then the method continues with step 64. The method ends when all map points 80 have been sized and rendered using embodiments described hereinabove.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method, comprising:
providing a processor;
receiving, by the processor, respective coordinates for multiple points on a surface;
rendering, by the processor, an image of the surface on a display screen; and
for each given point among the multiple points, computing, by the processor, a density of the points within a region surrounding the given point, and rendering, by the processor, on the display screen, the given point on the surface with a point size that is inversely related to the computed density,
wherein computing the density of the points within the region surrounding the given point comprises defining each given region as a sphere comprising a center having a center corresponding to the coordinates of the given point and a radius,
wherein the processor is adapted to vary the radius based on the density of the map points near the center of the sphere, wherein the processor is adapted to determine a geodesic distance to the closest point from the center, and wherein the density is directly related to the distance from the center of the sphere to the closest point.

2. The method according to claim 1, wherein computing the density of the points within the region surrounding the given point comprises counting a number of the points within the region.

3. The method according to claim 1, wherein computing the density of the given point within the region comprises identifying, from the multiple points, a further point that is closest to the given point, and determining a distance between the given point and the further point.

4. The method according to claim 1, wherein the surface comprises a two-dimensional surface or a three-dimensional surface.

5. The method according to claim 4, wherein the three-dimensional surface is representative of tissue in a body cavity, and wherein receiving the respective coordinates comprises receiving the respective coordinates from a medical probe inserted into the body cavity.

6. The method according to claim 5, wherein the body cavity comprises a heart, wherein the tissue comprises intracardiac tissue, and wherein the medical probe comprises an intracardiac catheter.

7. The method according to claim 1, wherein rendering the given point comprises presenting, on the display, the given point using a shape selected from a group consisting of a circle, an oval and a star.

8. The method according to claim 1, and comprising defining multiple visual effects, assigning each of the visual effects to a respective range of the densities, and rendering, on the display, the given point on the surface with a given visual effect that is based on the computed density.

9. An apparatus, comprising:
a display screen; and
a processor configured:
to receive respective coordinates for multiple points on a surface,
to render an image of the surface on the display screen, and
for each given point among the multiple points, to compute a density of the points within a region surrounding the given point, and to render, on the display screen, the given point on the surface with a point size that is inversely related to the computed density,
wherein computing the density of the points within the region surrounding the given point comprises defining each given region as a sphere comprising a center having a center corresponding to the coordinates of the given point and a radius,
wherein the processor is adapted to vary the radius based on the density of the map points near the center of the sphere, wherein the processor is adapted to determine a geodesic distance to the closest point from the center, and wherein the density is directly related to the distance from the center of the sphere to the closest point.

10. The apparatus according to claim 9, wherein the processor is configured to compute the density of the points within the region surrounding the given point by counting a number of the points within the region.

11. The apparatus according to claim 9, wherein the processor is configured to compute the density of the given point within the region by identifying, from the multiple points, a further point that is closest to the given point, and determining a distance between the given point and the further point.

12. The apparatus according to claim 9, wherein the surface comprises a two-dimensional surface or a three-dimensional surface.

13. The apparatus according to claim 12, wherein the three-dimensional surface is representative of tissue in a body cavity, and wherein the processor is configured to receive the respective coordinates by receiving the respective coordinates from a medical probe inserted into the body cavity.

14. The apparatus according to claim 13, wherein the body cavity comprises a heart, wherein the tissue comprises intracardiac tissue, and wherein the medical probe comprises an intracardiac catheter.

15. The apparatus according to claim 9, wherein the processor is configured to render the given point by presenting, on the display, the given point using a shape selected from a group consisting of a circle, an oval and a star.

16. The apparatus according to claim 9, wherein the processor is configured to define multiple visual effects, to assign each of the visual effects to a respective range of the densities, and to render, on the display, the given point on the surface with a given visual effect that is based on the computed density.

17. A computer software product, the product comprising a non-transitory computer-readable medium, in which program instructions are stored, which instructions, when read by a computer, cause the computer:
to receive respective coordinates for multiple points on a surface;
to render an image of the surface on a display screen; and
for each given point among the multiple points, to compute a density of the points within a region surrounding the given point, and to render, on the display screen, the given point on the surface with a point size that is inversely related to the computed density,
wherein computing the density of the points within the region surrounding the given point comprises defining each given region as a sphere comprising a center having a center corresponding to the coordinates of the given point and a radius,
wherein the processor is adapted to vary the radius based on the density of the map points near the center of the sphere, wherein the processor is adapted to determine a geodesic distance to the closest point from the center, and wherein the density is directly related to the distance from the center of the sphere to the closest point.

* * * * *